United States Patent [19]

Ashby

[11] 4,392,494

[45] Jul. 12, 1983

[54] LIGATURE TYING INSTRUMENT

[76] Inventor: Richard L. Ashby, 290 Crestmont Dr., Oakland, Calif. 94619

[21] Appl. No.: 250,104

[22] Filed: Apr. 2, 1981

Related U.S. Application Data

[63] Continuation-in-part of Ser. No. 12,004, Feb. 14, 1979, abandoned.

[51] Int. Cl.$^3$ .............................................. A61B 17/12
[52] U.S. Cl. .................................... 128/326; 128/321; 433/4; 433/159; 140/121
[58] Field of Search ............... 128/326, 340, 321, 335, 128/322; 140/149, 118, 121, 119, 123, 124; 81/428 R; 433/4, 159

[56] References Cited

U.S. PATENT DOCUMENTS

| | | | |
|---|---|---|---|
| 2,393,910 | 1/1946 | Karle | 128/340 |
| 3,393,680 | 7/1968 | Curutchet | 128/325 X |
| 3,420,280 | 1/1969 | Allyn | 140/149 |
| 3,577,991 | 5/1971 | Wilkinson | 128/340 |
| 3,621,890 | 11/1971 | Anderson | 140/123 |

FOREIGN PATENT DOCUMENTS 479719   2/1938   United Kingdom ................ 128/326

OTHER PUBLICATIONS

Trylon Surgical Instruments Catalog, p. B58 (1971) found in A.U. 335.

Primary Examiner—Michael H. Thaler

[57] ABSTRACT

This patent describes a new orthodontic instrument to be used for tying or twisting the ligature wires used to hold the arch wire to the bracket. It also explains the method of use which consists of: twisting the wires, after the ligature wire has been placed on the bracket; tucking the twisted end out of the way; and then breaking the end at the tip of the instrument. The instrument replaces three instruments normally used, by improvements in jaw design to facilitate grasping and centering the wires for spinning, balancing the instrument by general symmetry, and the addition of an extension handle to allow rapid spinning, and tucking of the wire ends as they are broken in a controlled manner, and at a specific place. The instrument thus simplifies, speeds and further improves the application of ligature wires.

5 Claims, 11 Drawing Figures

U.S. Patent   Jul. 12, 1983   Sheet 1 of 2   4,392,494
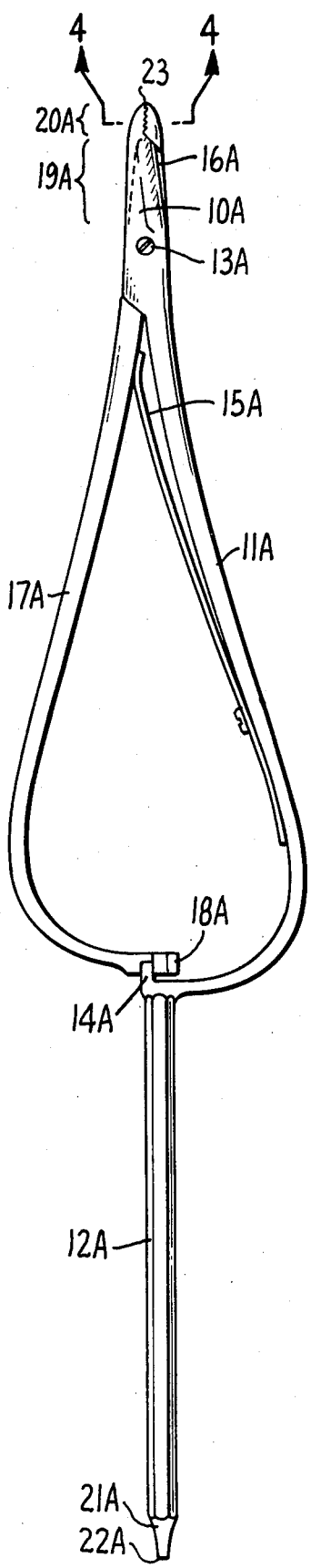
FIG. 1A.
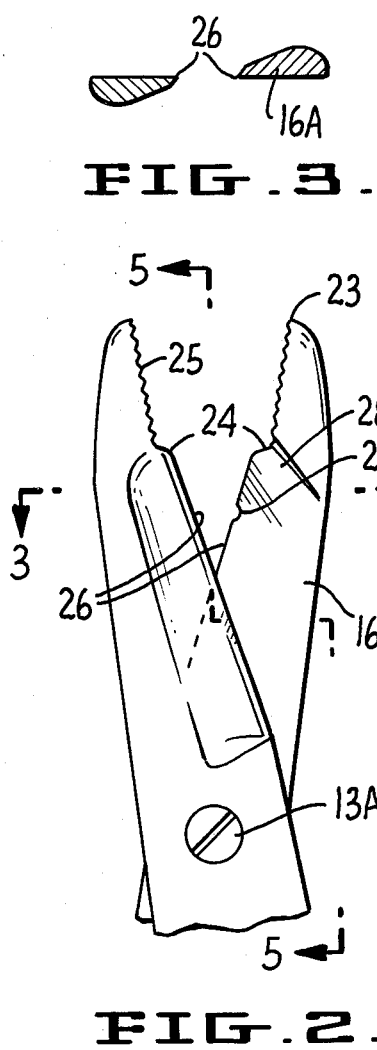
FIG. 2.
FIG. 3.
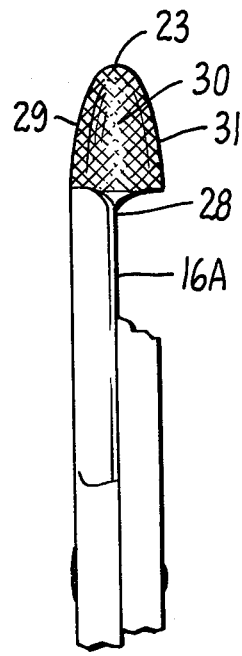
FIG. 5.
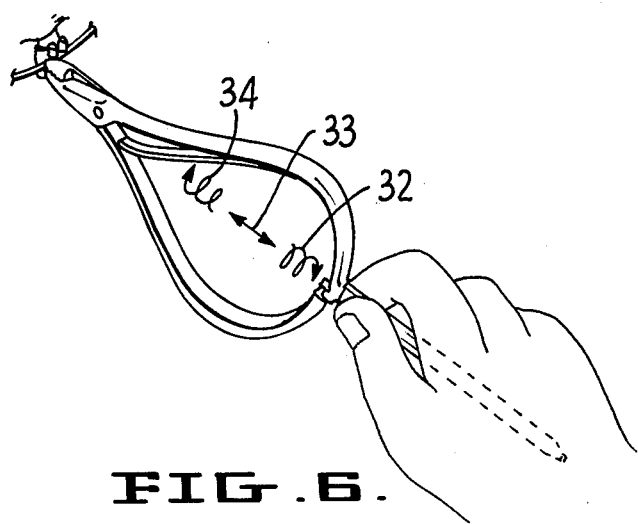
FIG. 6.

LIGATURE TYING INSTRUMENT

This is a continuation in part of my copending application Ser. No. 12,004, filed Feb. 14, 1979, now abandoned; and this contains material from the original application and new material not previously claimed. Reference is also made to my disclosure document #068679.

SUMMARY OF THE INVENTION

The object of the invention was to improve current means of securing the arch wire to the bracket as presently practiced in orthodontic therapy. The intention was to develop one instrument which could do the whole process. Thus saving time passing instruments back and forth between orthodontist and assistant.

The development of such an instrument resulted in modifications and improvements to the process of orthodontic ligation. To begin with the instrument was basicly a hemostat type plier of the mathieu style commonly used in orthodontics. The jaws were shortened and divided into two parts, a much smaller grasping portion at the tip and a wire guiding portion nearer the pivot, termed the laterally reduced portion. To facilitate the placement of the wires to be twisted a portion of the side of the jaw members was removed, forming a guiding surface rotated about 90 degrees from the plane of the face of the jaw members, the axis of rotation being that of the long axis of the instrument.

Curvature of the plane of the face of the grasping surfaces of the jaws is such that the part toward the tip is either conically or spherically concave, while that part closer to the pivot is cylindrically concave, further facilitated placement of the wires in the long axis of the instrument, and concentrated the force exerted on the wires toward the exact tip of the instrument. It also helped to prevent dislodgement of the wires from between the jaw members in a direction parallel to the general plane of the face of the jaw members.

However, a major improvement was achieved by the addition of an extension rigidly fixed to one of the handle members for the purpose of spinning, holding, pulling, and pushing the instrument in any non-conflicting combination, allowing greater control of the instrument and allowing the main portion of the instrument, in its modified form, to be used with out touching it. And then when required, to smoothly shift from the extension to the main part of the instrument and utilize it with out interference from or contact with the extension. Further improvement was achieved by shaping the extension to have a smooth surface with a polyagonal cross section, of between 5 and about 12 surfaces, a cross sectional dimension approximating a fifth of an inch to facilitate spinning, and a length just greater than the distance from the center of the palm of the hand to the tips of the index finger and thumb when finger and thumb contact. A further improvement was made by tapering the tip for comfort in the palm of the hand and to act as a rotational pivot point in conjunction with the wires at the tip of the instrument for rotation around the long axis. An instrument balanced about the long axis and substantially symetrical, having its end flattened for use as a pushing end when the instrument is reversed end for end in the hand.

BRIEF DESCRIPTION OF THE SEVERAL VIEWS OF THE DRAWINGS

FIG. 1A shows a side view of the complete instrument in its preferred form when it is locked in the closed or grasping position.

FIG. 2 shows an enlarged side view of the open jaws.

FIG. 3 shows a cross section taken at line 3—3 of FIG. 2.

FIG. 5 is a plan view taken at line 5—5 of FIG. 2 showing the concave face of the grasping portion of the jaw, and the side or laterally reduced part of the jaw.

FIG. 6 shows how the instrument is held and used in the hand for twisting, tucking, and breaking.

Figure 4A:
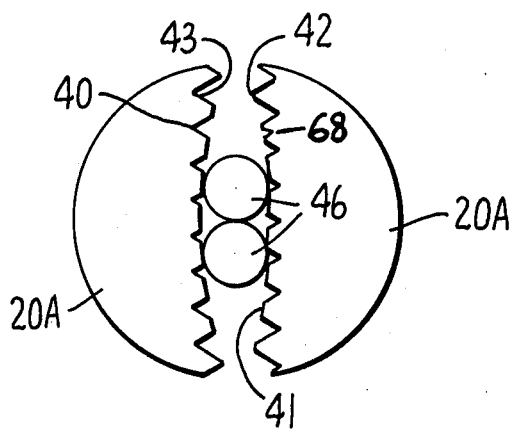
FIG. 4A is a diagramatic cross section taken at line 4—4 of FIG. 1A showing one type of interlocking serrations and wire position.

The present invention relates generally to a dental device primarily intended for use in the practice of orthodontics, but not limited there-to. It is forseen that it would be of use in hard and soft tissue surgery, attaching soft tissue together, bones together, soft tissue to bone, stabilization of implants, fixation of jaws in fractures, other oral surgical procedures, periodontal surgery, including fixation and splinting of teeth, hobby and craft application, decorating, flower arranging, flytieing, electrical wiring, and wire splicing, and in general any operation which does one or more of the following: twists wires, positions wire ends, or breaks or cuts wires.

I shall now briefly describe the action of the instrument as it is generally used in orthodontics:

Note that the term 'tie' as used in orthodontics means the twisting of fine wires called ligature wires. The terms ligate and ligature also refer to this tying process or twisting of the wires securing their position.

The shape and structure of this new device or instrument is such as to allow it to do three main functions normally done by three separate instruments, namely: (1) tighten, twist and tie the ligature wire, (2) tuck the end of the ligature or tie wire, and (3) break off the end of the wire at the right length. The unique design of this instrument is such as to allow to be performed in one continuous and smooth operation, these three fore mentioned functions.

Once these methods of operation and use of this instrument are understood, it will be evident that a new and useful instrument has been invented. That its use in combination with the new method will perform not only the three mentioned functions in a very rapid manner, but with ease and accuracy permitting a previously complex operation to be performed with safety and speed; and allow the average dental assistant to perform the tying function with minimum training and experience.

In addition there are advantages to the patient that will be pointed out later that are primarily the result of the practicality, with this instrument, of completing the whole operation on each ligature at one time, instead of using one instrument to do the twisting, another instrument to do the cutting of the end of the ligature wire, and still another instrument to tuck the end of the ligature under the wing of the bracket or under the arch wire out of the way.

In the prior state of the art several different types of ligation and ligating instruments are being used, these fall into several categories.

The first category includes stretching and twisting instruments of which type the coon ligature tying instrument is typical. In these instruments the ligature wire after having been placed over the arch wire and under the wings of the brackets, is stretched through the grooved tips of the instrument. The ligature ends are usually secured by some means at the pivot point of the plier-like-instrument in which, as the handle is squeezed, the tips are spread apart and the ligature is thereby tightened around the bracket. The instrument is then rotated in the ligators hand to twist and wrap the wire. With this device a separate cutting operation and a separate tucking operation with separate instruments are required. This is usually done after all the brackets have been ligated. In addition to being time consuming, this instrument requires a high degree of skill in the operators hands, and many instruments are involved. It has the further disadvantage of having multiple ligature ends protruding from the patients mouth, until a cutting operation, which leaves very sharp ends, is followed by the tucking operation. Because the tips of the instrument are spread apart during the tightening operation, the tips can not be close to the bracket during the twisting operation. This is not a procedure conducive to patient comfort, and cheek or lips may be pinched between the instrument and the bracket or arch wire. Any of the ends of the wires that eventually protrude from under the ends of the wings of the brackets, having been cut by a sharp instrument, have a razor sharp edge to irritate the lips and cheeks.

The second type of tying instrument in common use is the mathieu ligature tier. This instrument is a type of hemostat and has the basic improvement over the preceding instrument that it clamps the two ends of the ligature wires together for the twisting operation, resulting in the tips of the jaw members being close together and therefore some what easier to control; however, this instrument also requires a high degree of hand dexterity and skill which is typical of the preceding instrument. Due to its width, it is difficult to control the tip position and twist the handles at the same time, and has to be followed again by the cutting and tucking operation involving separate instruments. Little rotation momentum can be developed with this instrument.

A third category of instrument, the stevens ligature holder, utilizes a clamping mechanism but with one of the handles very short, and the other handle straight and long, this handle is suitable for twisting except the instrument is not symmetrical. The junction of the jaw members in the closed position is not in line with either handle but is in line with the bisection of the angle of the handle members. As a result of the lack of symmetry and imbalance, the tip wobbles severely. This instrument does utilize a clamping action to hold it closed, as does the preceding instrument, but the lack of symmetry will not allow the build up of rotational inertia; therefore, it requires that all of the twisting action be done by the fingers, and any attempt at fast rotation results in excessive wobble and inaccurate winding or tying. The wobble also interfers with using this instrument for breaking the wire and tucking it, since it will not allow a uniform build up of stress at the tip of the jaw members. Because of a circular whipping action, the wire is wound up (that is the twisted pair is coiled in spring-like fashion) frustrating the breaking. As a result of uncertainty in where and when the wire will break, a tucking action is also not possible.

The Stevens device is quite similar in shape, form and use with the Anderson wire dressing tool, U.S. Pat. No. 3,621,890, the main structural difference being the cylindroidal channel in one or both of the jaw members. It should be noted that the structural difference makes a large functional difference when compared with the present invention. His urging of the wires toward the midline is the result of the twisting action and the spring action of the jaw members not the cylindroidal channel, since there is no urging without rotation. Another difference with the present invention is that in Anderson's device the winding of the wires occurs within the jaws while in my device the winding or twisting occurs out side of the jaws. It is doubtful that the Anderson device would twist wires which had not previously been twisted, especially if only two wires were to be twisted.

Both of these last two devices have no symmetry about the long axis which would allow spinning without wobbling. With the Stevens instrument it might appear that it is somewhat capable of similar action to the present invention, but in reality and in use, it is not. This instrument also lacks a tapered end on the extension or long handle, and as a result, the instrument could not be suspended between the wires at the tip of the jaws and the hand as it supports the tip of the handle in the palm of the hand, in such a manner suitable for spinning. Orthodontists using this instrument still do separate cutting and tucking operations.

The preceding instruments have another disadvantage overcome by the present invention. That is the design of the tips which grasp the wire. Since the preceding instruments have both jaw members relatively broad and extending back close to the fulcrum point, it is difficult to engage and clamp both ends of the ligature wire in a suitable manner for twisting. In the present device the tips of the jaw members are wide only at the ends, for grasping, and then each jaw member is shaped in such a manner to allow both ends of the ligature wire to be conveniently and observably placed between the tips of the jaw members, in a central position, before grasping; regardless of which handle member is up in the operators hand.

The present invention solves all the above problems in the best method brought forth so far. As I describe the various parts of the above mentioned ligature typing instrument and the manner in which it interacts with the ligature wire, it will be seen that a new and useful invention has been created along with a process and method for its use, which is superior to any method presently in use; and that this invention is the result of a combination of a number of factors never before brought togehter in a ligature tying instrument.

These factors are: (1) a clamping action, (2) a locking mechanism, (3) a basically symetrical instrument, one which is balanced to allow ease of spinning and in general freedom from vibration, (4) a longer handle projecting in the line of general symetry, such that its end is tapered or other formed to act as a pivot to form a rotatable support for the instrument when the end is held against the palm of the hand, (5) sufficient mass at the right distance from the midline to be able to rapidly develop sufficient rotational inertia (within about a quarter turn) to result in the necessary 4 to 8 twists of the ligature wires, (6) a lightness in the hand without central bulk, (7) a suitable size for easy hand manipulation for the clamping and twisting operation, (8) jaws designed to allow easy placement of the ligature wires to be clamped and jaws which urge or otherwise force the wires toward the long axis of the instrument, both during grasping and also during pulling, pushing, rotation, and side to side motion of the instrument, jaws who's faces have intermeshing serrations in which the faces are concave, for the purpose of accommodating a larger range of wire sizes, jaws which exert additional pressure on the wires right at the tip in order to facilitate breaking the wires at that point, (9) a quick release feature once the operation is complete, (10) a tip and handle shape conducive to rapid removal of the ends of the ligature wire to be disposed, (11) an instrument having essentially two handles, and (12) a long central handle allowing for a pulling motion to be changed to a pushing motion without interfering with the rotational movement involved in the twist-operation. This last mentioned feature allows for the tightening of the ligature and the rapid build up of stress at the approximate tip of the typing instrument due to the continued rotation and the approximately right angle formed when the pulling and twisting operation is changed to a pushing and twisting operation when the tip of the jaws is simultaneously allowed to move to the side of the axis or line in which the wires were previously being twisted.

This allows the breaking of the twisted ends at the proper point resulting in a tucked end that does not require cutting. Futhermore it produces an end which is not sharp and is slightly reduced in size due to the 'twist off' effect.

It was the insight that the combination, in a single instrument, of the above mentioned attributes would allow the twisting, tucking, and breaking operations to be done in one continuous rapid motion, that is unique about this invention.

In order to realize why this present invention is such a practical and useful device, it is necessary to understand in detail the exact method of use, which is in general as follows:

The present invention is intended to be used with pre-shaped ligatures of the standard form and size, except approximately one-half the standard length. This is desirable to facilitate the removal of the ligature from the instrument following the break-off, and has the economic advantage of saving ligating wire used by previous instruments.

The ligature wire is placed over the arch wire and around the wings of the bracket in the usual manner by the left hand. The instrument is held with the jaws slightly apart usually about 2 to 3 millimeters. In this position the shear edges of the scissor portion of the jaws are still closed beyond their cutting position due to the unique shape, which portion is "dip safe". In this position and with this preferred instrument, one side of the one scissor, which is the laterally reduced portion of the jaw member, is positioned against the wires. With the portion of the wires which extends toward the bracket positioned between the grasping faces of the jaws, a pivoting movement of the instrument about a line perpendicular to the the grasping face of the jaw and extending through the long axis of the instrument and lying in the plain of the laterally reduced portion of the jaw where it joins the grasping portion of the jaw, allows centering of the wires where they extend from the tip of the jaws. At this time the handles are squeezed engaging the locking teeth 14A and 18A grasping the wires in the long axis of the instrument.

With the jaws secured on the ligature wires at a distance of about 2 millimeters from the bracket, the right hand is slid from handle members numbers 17A and 11A to the handle extension member number 12A, which is then held between the thumb and index finger. With slight tension on the ligature wires, the handle extension number 12A is spun, turning the whole instrument: the ligature wire being thus twisted tight in the section between the bracket and the tip of the jaw members and twisted loosely in the opposite direction around the outside of the jaw members in the section between the jaw members and that part held in the left hand, until the left hand releases its grip, thus keeping the ends of the wires out of the way and away from the face. It is as if the instrument were between two pivot points, suspended on its long axis. One pivot point being the wires being twisted at the tip of the jaw and the other pivot point being the end of the extension handle resting in the palm of the hand. Between these two pivots the instrument is relatively free to turn around its long axis when so urged by the finger and thumb. With this in mind, it is easier to understand why balance and symetry are very important to its proper action. At this time the handle extension is pushed forward and slightly to one side, in the direction of the wing of the bracket and the underneath side of the arch wire, performing the tuck operation. During this maneuver the rotation continues, resulting in a concentration of stress at the exact tip of the jaws where continued rotation results in reduction of the wire diameters and breakage occurs.

The left hand or an assistant now grasps the jaw portion and the ligature wire remaining with the instrument, while the right hand shifts from the handle extension number 12A to the handle portions number 17A and 11A and upon squeezing the later members now unlock the jaws and releases the wire as the teeth numbers 14A and 18A now move out of contact. Then number 14A now passes on the other side of teeth number 18A, as the grip is slowly released spring 15A separates the handle and jaw members, and the operation is complete.

Other factors and structure contributing to the unique action of this instrument are: the length of the extension handle, which should be just greater than the distance from the center of the palm of the hand to the tips of the index finger and thumb, when the finger and thumb contact. It should be in cross section about a fifth of an inch, because this size can be rolled between the thumb and index finger with the palm side of the finger and thumb just passing. Larger diameters do not allow increased finger-thumb pressure to secure the handle by completely encompassing it in the pads of the finger and thumb. They also have the disadvantage that as the cross sectional dimension increases the number of rotations of the instrument for the displacement of the tips of the fingers is decreased, making the instrument less effective. Also the end of the extension handle must be tapered conically to improve the spinning and lessen the friction as it turns in the palm of the hand. A small ball bearing could be installed at the end for the same purpose, but there is greater utility in having the end squared off for auxiliary tucking operations.

The extension handle should be of polyagonal cross section, having more than four sides with the preferred model having eight sides.

At first it may seem that there is a conflict in the construction of the instrument as described, in that as the wires are grasped in the tip of the instrument, theoretically there should be no contact with the faces of the grasping surfaces except at the exact tip 23 of FIGS. 1A, 2, and 5; in reality the instrument works because the exact tip 23 is further away from the pivot than the rest of the grasping face, there is some slight bending and flexibility of the jaw members, and there may be some slight play in the pivot.

While the described action of the instrument may seem complex, in reality and practice it is an extremely fast and efficient operation which no other instrument can perform, due to the unique design and incorporation of: the proper tip length and shape, automatic ligature centering action of the tips, both before grasping and by the action of the laterally reduced portion and also by the concavity of the face of the grasping portion of the jaw members upon grasping, lip safe design, smooth un-encumbered handles, suitable securing and release mechanism, proper weight, rotational momentum, relatively symmetrical design, spinning handle, which is the extension handle, and an auxiliary tucking tip and scissors with one scissor blade notched in a rounded manner, (rarely used).

While I have shown only one preferred form of my invention it is understood that the present invention may be quite varied. For example with or without the scissor portion and still be "dip safe". The method of use will vary slightly according to the particular ligature tyer style. A number of these various styles have been made and utilized while developing the preferred form of my invention.

While I have shown mainly the preferred form, it should be understood that the various changes or modifications can be made within the scope of the claims here to attached without departing from the spirit of the invention.

DETAILED DESCRIPTION OF THE DRAWINGS

Referring now to FIG. 1A, it will be seen that the instrument is comprised of a pair of jaw members 10A which includes a grasping portion 20A and a scissor portion 19A. 19A will also be referred to as the laterally reduced portion, in instruments without a scissor. The handle portion includes the main handle members 17A and 11A, a spring 15A, and a locking/releasing portion comprising teeth of a ratchet nature on the end of 17A, and an intermeshing tooth 14A on the end of 11A. Between the jaw and handle member is a pivoting member 13A. Attached to 11A is an extension handle 12A which is a rod of octagonal cross section with a tapered end 21A and a flattened tip 22A. 16A is a flattened surface and the innermost surface of 19A.

FIG. 2 is an enlarged view of the jaw portion of the instrument with the jaws apart to show 25 which is in general the face of the grasping portion of the jaw members, or for sake of convenience will, throughout most of the patent, just be called the face of the jaw. 23 is the tip of the jaw member where the face of the jaw 25 meets the outer curvature. 24 indicates the manor in which the edge of the scissor is raised above the general plane of the face of the jaw 25. 26 is the edge of the scissor, 27 is a notch in the edge of 26. 28 is the area or groove where the grasping portion of the jaw joins with the laterally reduced portion, or scissor portion of the jaw, 16A is the plane of the laterally reduced portion of the jaw.

FIG. 3 is a cross section of FIG. 2 at points indicated, following the line of 3—3 in FIG. 2. 26 shows the edges of the scissors in the preferred form, and 16A shows the laterally reduced portion or plane.

BRIEF DESCRIPTION OF FIGS. 4A, 4B, 4C, 4D, AND 4E

FIGS. 4A, 4B, 4C, 4D, and 4E show diagramatic drawings of the cross section taken across the tip of the jaw following the line 4—4 in FIG. 1A.

FIG. 4A shows one of the two preferred forms. The depth of the serrations forms a straight line 40, the tops of the serrations forms a concave arc 41, and interlocking serrations are indicated by 42, and 43. The wires being grasp and twisted are shown by 46.

Figure 4B:
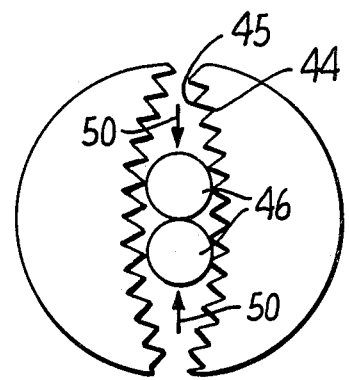
FIG. 4B is a diagramatic cross section taken at line 4—4 of FIG. 1A showing the preferred type of serrations.

FIG. 4B is a second preferred form showing serrations with a curved base 44 and curved tips 45. Arrows 50 show the direction the wires 46 are urged by the tips of the serrations upon grasping.

Figure 4C:
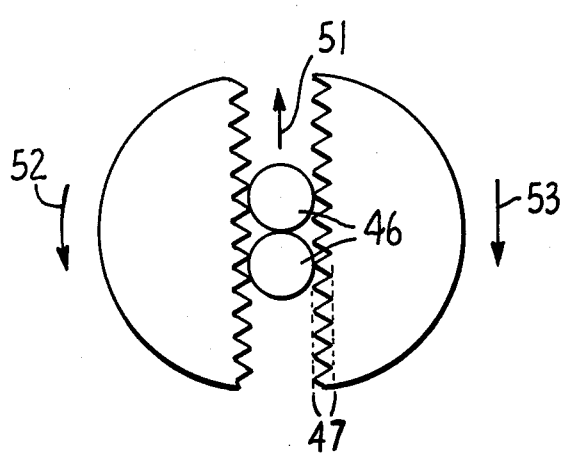
FIGS. 4C, 4D, and 4E are diagramatic section used to teach the inventive art.

FIG. 4C shows serrations where serration tips and bottoms are straight lines 47. Arrow 51 shows the direction wires are urged when instrument moves in direction of arrow 53, or in direction of arrows 53 and 52.

Figure 4D:
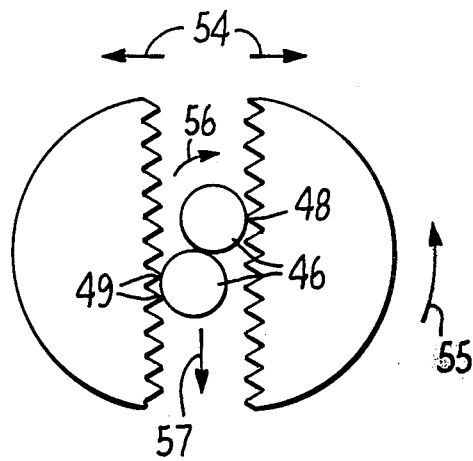
Figure 4E:
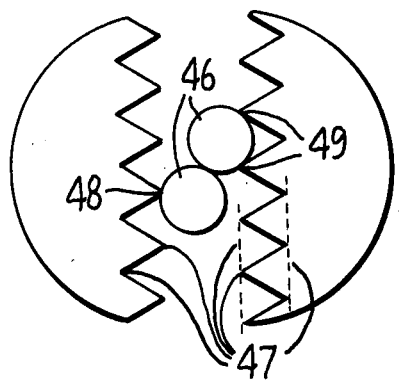

FIG. 4D shows tendency for jaws to separate, arrows 54, upon rotation, arrow 55. Rotational tendency due to resilience of wires arrow 56, tendency for wires to be displaced arrow 57, due to fewer contact points 49 and 48 with the jaws. FIG. 4E shows the effect of increasing the size of the serrations.

DETAILED DESCRIPTION OF FIGS. 4A, 4B, 4C, 4D, AND 4E

Note that FIGS. 4A, 4B, 4C, 4D, and 4E are all diagramatic drawings.

Referring now to FIG. 4A which is a diagramatic drawing of the cross section across the jaw member of FIG. 1A, it will be seen that the jaw members are serrated and that there is a slight concavity of the tips of the serrations, which slight concavity would extend in general in the long axis of the instrument, except that as the concavity extends toward the exact tip of the instrument, the slight concavity diminishes to nothing at the exact tip of the instrument. See the exact tip of FIG. 1A, No. 23. Furthermore, the serrations may take several variations, such as shown in FIGS. 4A and 4B, 4B is preferred. FIG. 4B shows the serrations such that serrations on opposite jaw halves interlock upon closure of the jaws such that the degree of interlocking determines the degree of closure, which interlocking interfers not at all with the slight concavity of the jaw members and the interaction of the interlocking with the slight concavity extends the range of the diameter of the wires which can be twisted and still be suitably accommodated by the instrument. It will be seen and understood that when small diameter wires are used, over lapping of the peripheral edges of the face of the jaw members will occur, due to the interlocking of the serrations. This interlocking will occur progressively less as the diameter of the twisted wires increases. The lack of any concavity at the exact tip increases the gripping pressure on the wire at this point No. 23 in FIGS. 1, 2 and 5 and further aids the parting or breaking process, and helps to insure that the break occurs at the exact tip of the instrument.

Referring now to FIG. 4B it will be seen that the slight curved jaw surfaces are serrated to a uniform depth, such that serrations are completely formed, as opposed to those shown in FIG. 4A. And such that the tips of the serrations No. 45 and the depths of the serrations No. 44 both form equal archs. As to be discussed later, it is not necessary that both arcs be equal or that the serrations be uniform.

Arrows of FIG. 4B, No. 50 show the general direction the wires are urged upon closure of the jaws, as the slight curvature allows more space in the mid-line or long axis position, and less room toward the peripheral edges. It is to be understood that this effect is due to the slightly curved jaw faces and not the serrations, and as a result this effect would also be observed with any concavly curved jaw faces including those of FIG. 4A. This is a very important part of my invention because through this means the wires as they are being twisted maintain their centered position in the instrument, thereby maintaining the balance of the whole instrument as it is being spun, thus preventing wobble, and most importantly preventing loss of grip on the wires altogether, as can occur if designed as in FIGS. 4C, 4D, and 4E.

Referring now to FIG. 4C it will be seen that in this figure the jaw faces are essentially flat, except for the serrated surface and whether serrated as shown or not serrated, the effect of having no shape or force urging the wires to the center position of the jaw surfaces or faces, is that the slightest imbalance during rotation, wobble, or side to side movement of the jaws in the direction of arrow 53 or reverse direction will result in movement of the wires in the opposite direction, arrow No. 51, in relation to the jaws.

Thus with flat jaw faces the effect is that the twisting of the wires and the speed of use and action of the instrument is interferred with, which in the extreme results in loss of grip on the wires. Arrow No. 52 depicts rotation that usually accompanies the lateral movement of the jaws depicted by arrow No. 53. If in addition to the twisting action of the instrument, the instrument is also concurrently being pulled, arrow No. 32 of FIG. 6, the effect of the lateral displacement of the wires in the jaws will be increased, and a further increase in lateral displacement will occur if the pulling also results in slippage of the wires in the grip of the jaw faces, since static friction is greater than the friction of two parts once sliding has commenced.

The maximum lateral displacement effect on the wires however is observed to occur when the instrument is pushed, arrow No. 34 of FIG. 6 in the handle to jaw direction, and when at the same time the tip is being forced in either direction in the plane of the face of the jaw members as shown by arrow No. 53 of FIG. 4C. It is also to be observed that there are four or more points of contact between the wires and the jaw faces. Each wire has two or more contacts, at least one with each jaw face. In contrast the curvature in my invention, FIGS. 4A and 4B, that is the concavity of the face of the jaw members, acts throughout the complete operation of the instrument to prevent displacement of the wires and to correct it if it does occur.

Referring now to FIG. 4D it is seen that as a generally flat faced jawed instrument is rotated, one wire is forced harder against one jaw face than it is forced against the opposing jaw face, this is because the jaws tend to be forced apart, arrows 54, due to the resistance to twisting of the wires arrow 56, as the instrument is rotated in direction of arrow 55. Contact of the jaw faces with the wire may thus be reduced to only one or two points, Nos. 49 and 48 respectively with each wire only contacting a single jaw as shown in the diagramatic cross section of FIG. 4D. It should be pointed out at this time that any device, such as the allyn device, in which the rotation of the device is caused by a pulling motion, will, when the pulling motion is terminated in order to start a pushing motion, even if the pushing motion also causes a rotation in either direction, cause a loss of rotation and rotational torque for an instant, at which time the wires would be less firmly gripped and more susceptible to lateral displacement as previously mentioned and as indicated by arrow 57 of FIG. 4D. The tendency for the jaws to separate upon twisting causes the resistance to lateral displacement along the face of the jaw members to further diminish resulting in a greater tendency to displacement or loss of grip on the wires.

Referring now to FIG. 4E it will be seen that by increasing the size of the serrations and decreasing their number, the problem of lateral displacement of the wires is partially solved, except that in doing so, centering of the wires in the jaw members may or may not be possible, depending upon the diameter of the wires, and the size and spacing of the serrations and the relative position of the serrations in relation to the center, or longitudinal midline of the jaw faces. Also, while lateral displacement is less if the wires are off axis when grasp, at best they stay off axis causing wobble, and twisting irregularities resulting in a less efficient instrument.

It will now be seen that the slight concavity of the face of the jaw members can be thought of as a single large serration, centrally placed on the face of the jaws upon which the smaller serrations are placed, or as a compounding of serrations.

In any event the method of maintaining the central position of the wires in the jaw members is best achieved by the improvement of this patent by one of the methods as previously described and shown in either FIG. 4A or 4B. And that on the basis of compounding serrations previously mentioned, the individual serrations of FIG. 4A could be finely serrated 68, or the size and depth of the serrations could change going from mid surface to edge.

FIG. 5 shows a plan view taken 90 degrees to FIG. 2 and from the points indicated, following the line 5—5 in FIG. 2. As indicated before, 16A shows the lateraly reduced portion to be a plane containing the long axis of the instrument. 23 shows the tip of the jaw member. 28 shows the junction between grasping portion of the jaw and the laterally reduced portion of the jaw 16A. 28 may also be described as an angle or grove. 29 is one side of the grasping face. 31 is the other side of the grasping face, and 30 is the central part of the grasping face, in which 30 is below the plane containing 23, 29, and 31, such that the face of the jaw 25 from 30 toward 28 is that of a cylinder, while the surface of the jaw from 30 toward 23 is conical, follows the curvature of a section of a cone, or is spherical.

FIG. 6 shows the hand position of the instrument during the twisting, tucking, and breaking operations. Arrow 32 indicates that for twisting the wires the instrument is pulled as it is being spun. Arrow 33 indicates that the instrument can be changed from pulling to pushing independently of the rotation. And arrow 34 indicates the pushing-spinning motion used for tucking and for breaking.

Figure 7:
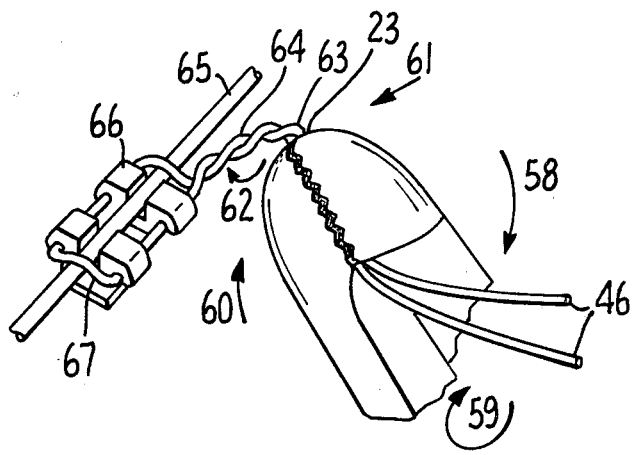
FIG. 7 shows how the tip of the jaw of the instrument is positioned in relation to the twisted wires when ready to break the wires.

Referring now to FIG. 7 it will be seen that it shows the working relationship between the grasping portion of the jaw 20A, arch wire 65 lying in the orthodontic bracket 66, and different places along the ligature wire 67, 64, and 46 being placed, to attach the arch wire 65 to the bracket 66, arrow 58 and 60 show rotation of the tip 20A to place a bend in the twisted wires 64, at 63, arrow 59 shows that rotation about the long axis of the instrument is still taking place, arrow 61 shows that for an alternate tuck position (of the broken ends of the wire, other than at 63) the tip 23 can be allowed to move toward the bracket by the spinning around the long axis, arrow 59, such that it moves in direction of arrow 62, and thus contacts the twisted wires at position 64. Note that the twisted wires are forced to form approximately a 90 degree angle at the tip of the instrument, and this is the place at which the wires will break.

I claim:

1. An improvement in ligature tying instrument comprising a hemostat-like plier in which grasping jaw members are flexibly pivoted together intermediate their ends; means for releasably securing said jaws in grasping position on a ligature wire;

wherein the improvement comprises a balanced and substantially symmetrical instrument having one handle member extended as a polygonal rod rigidly fixed in the long axis of the instrument for purposes of spinning the instrument about a longitudinal centerline, when said instrument is locked in the grasping position;

wherein the grasping face of the jaw members is concave except right at the tip, such that closure of the jaws tends to force the grasped wires toward the long axis of the instrument for purposes of centering the wires and maintaining their central position during the twisting, tucking and breaking process.

2. An instrument as in claim 1; wherein, the grasping faces of the jaw members are serrated such that the peaks of the individual serrations would lie in a concave surface.

3. An instrument as in claim 1; wherein, the face of the grasping portion of the jaw member has serrations which are serrated, forming a compounding of serrations.

4. An instrument as in claim 1; wherein, the general contour of the face of the grasping portion of the jaw member is cylindrical in part and conical in part, whereby increased pressure is applied at the tip of the jaw member allowing twisted wires to be broken at the tip in a controlled manner.

5. An instrument as in claim 1; wherein, the general contour of the face of the grasping portion of the jaw member is cylindrical in part and spherical in part, whereby increased pressure is applied at the tip of the jaw member allowing twisted wires to be broken at the tip in a controlled manner.

* * * * *